(12) United States Patent
Brill

(10) Patent No.: US 7,184,152 B2
(45) Date of Patent: Feb. 27, 2007

(54) OPTICAL MEASUREMENTS OF LINE EDGE ROUGHNESS

(75) Inventor: Boaz Brill, Rehovot (IL)

(73) Assignee: Nova Measuring Instruments, Rehovot (IL)

(*) Notice: Subject to any disclaimer, the term of this patent is extended or adjusted under 35 U.S.C. 154(b) by 214 days.

(21) Appl. No.: 10/513,034

(22) PCT Filed: Mar. 4, 2003

(86) PCT No.: PCT/IL03/00167
§ 371 (c)(1),
(2), (4) Date: Nov. 1, 2004

(87) PCT Pub. No.: WO03/075041
PCT Pub. Date: Sep. 12, 2003

(65) Prior Publication Data
US 2005/0195413 A1    Sep. 8, 2005

(51) Int. Cl.
G01B 11/30    (2006.01)

(52) U.S. Cl. ..................... 356/636; 356/600

(58) Field of Classification Search .. 356/237.1–237.5, 356/625–631, 600–614
See application file for complete search history.

(56) References Cited

U.S. PATENT DOCUMENTS

| | | | |
|---|---|---|---|
| 6,873,938 B1* | 3/2002 | Paxton et al. | 702/188 |
| 6,370,680 B1* | 4/2002 | Nguyen | 716/19 |
| 6,516,528 B1* | 2/2003 | Choo et al. | 33/552 |
| 6,539,331 B1* | 3/2003 | Fiekowsky | 702/159 |
| 6,697,153 B1* | 2/2004 | Wright et al. | 356/237.4 |
| 6,909,791 B2* | 6/2005 | Nikitin et al. | 382/108 |
| 6,976,240 B2* | 12/2005 | Chang | 716/19 |
| 2002/0018217 A1* | 2/2002 | Weber-Grabau et al. | 356/601 |

* cited by examiner

*Primary Examiner*—Hoa Q. Pham
(74) *Attorney, Agent, or Firm*—Dekel Patent Ltd.; David Klein

(57) ABSTRACT

A method and system for optical measurements of line edge roughness (LER) of patterned structures based on illuminating the structure with incident radiation and detecting a spectral response of the structure, and further applying software and/or hardware utilities for deriving information representative of said line edge roughness parameter/s from said spectral response of the structure.

13 Claims, 7 Drawing Sheets

OPTICAL MEASUREMENTS OF LINE EDGE ROUGHNESS

FIELD OF THE INVENTION

This invention is in the field of measurement techniques, and relates to optical systems and methods for accurate measurement parameters of patterned structures. The invention is particularly useful for controlling semiconductor manufacturing process.

BACKGROUND OF INVENTION

Lithography is widely used in various industrial applications, including the manufacture of integrated circuits, flat panel displays, micro-mechanical systems, micro-optical systems etc. Generally speaking, the lithography process is used for producing a patterned structure. During the manufacture of integrated circuits, a semiconductor wafer undergoes a sequence of lithography-etching steps to produce a plurality of spaced-apart stacks, each formed by a plurality of different layers having different optical properties. Each lithography procedure applied to the wafer results in the pattern on the uppermost layer formed by a plurality of spaced-apart photoresist regions.

To assure the performance of the manufactured products, the applications of the kind specified above require an accurate control of both the dimensions of sub-micron features of the obtained pattern and the roughness of the lines. The most important parameter for lithography, usually termed "critical dimension" (CD), is the smallest transverse dimension of the developed photoresist, usually being the width of the finest lines or the width of the smallest spaces between lines. Since the topography of the measured features is rarely ideal additional information found in the height profile, such as slopes, curves etc., may also be valuable in order to improve the control of the fabrication process. However, the shape of the lines in never identical when looking at different locations along the lines nor between different lines. For a full description it is therefore required to treat the line profile (even it for simplicity, we focus only on one profile parameter, e.g. the CD at the bottom of the line), as an ensemble of values rather than a single value. There are accordingly two kinds of measurements that can be done: a local measurement, relevant only to a specific line at a specific point along the line (such as usually done by e.g. CD-AFM or CDSEM), and an average measurement that averages some area along the lines and including several such lines (such as done by optical methods). When using a measurement that samples an area, such as optical methods, it is usually assumed that the measured value is some average of the specific local values. In many cases measuring the average value is sufficient or even advantageous over measuring local values, as it is assumed that most macroscopic process parameters affect the average profile while the noise contained in the local measurement due to line edge roughness (LER) is better averaged out However, the LER can be ignored as "noise" only as long as it is much smaller than the average profile parameters. If LER becomes a significant fraction of the CD, as may happen, for example, if average CD is reduced while LER is kept at its original magnitude (see FIG. 1), or due to some microscopic property of lithography process that promotes a large LER, than LER become an important characteristic of the process that has to be monitored. As shown in FIG. 1, the same line edge roughness (LER) is added to two different lines with different average CDs, $CD_1$ and $CD_2$ accordingly.

The ratio of the thinnest to the widest point is obviously making the LER a major issue for the thinner line whereas it may be ignored for the wider line.

Since LER is basically a complementary ("error bar") measurement to CD measurement, it would be advantageous to have the two being measured within the same tool. Such a measurement would be relatively straightforward for a SEM, which measures local values, however not as simple to an optical measurement tool (Scatterometry), that by nature measure average values over an area. In this invention we describe several ways by which an optical tool, can be utilized or enhanced in order to measure LER.

SUMMARY OF THE INVENTION

It is accordingly a need in the art to improve the optical measurements on patterned structures by providing a novel method and system for measurements in a sub-micron patterned structure to determine line edge roughness (LER), utilizing optical measurement tools comprising software and/or hardware utilities for deriving information representative of LER parameter/s.

It is a still further feature of the present invention to provide a system whose operation is fast enough, so that every wafer in the production line can be measured, allowing a closer control over the process.

The main ideas of the present invention are based on two basic modes of operation, i.e. "bright field" and "dark field" modes that an optical system may operate in. "Bright Field" (BF) mode of operation is characterized by the fact that while measuring an ideal structure, that does not include any LER, a substantial signal is being measured, while in "Dark Field" (DF) mode of operation an ideal sample would not produce any signal save of system background and noise. Accordingly, while in BF mode the methods described below aim to separate the effect of the LER on the measured signals from that of the ideal structure, in DF mode most of the signal can be attributed to imperfections such as LER, simplifying the detection and quantification of LER.

BRIEF DESCRIPTION OF THE DRAWINGS

In order to understand the invention and to see how it may be carried out in practice, several different preferred embodiments will now be described, by way of non-limiting examples only, with reference to the accompanying drawings, in which.

DETAILED DESCRIPTION OF A PREFERRED EMBODIMENT

LER Detection Methods in Bright Field Mode

Figure 1:
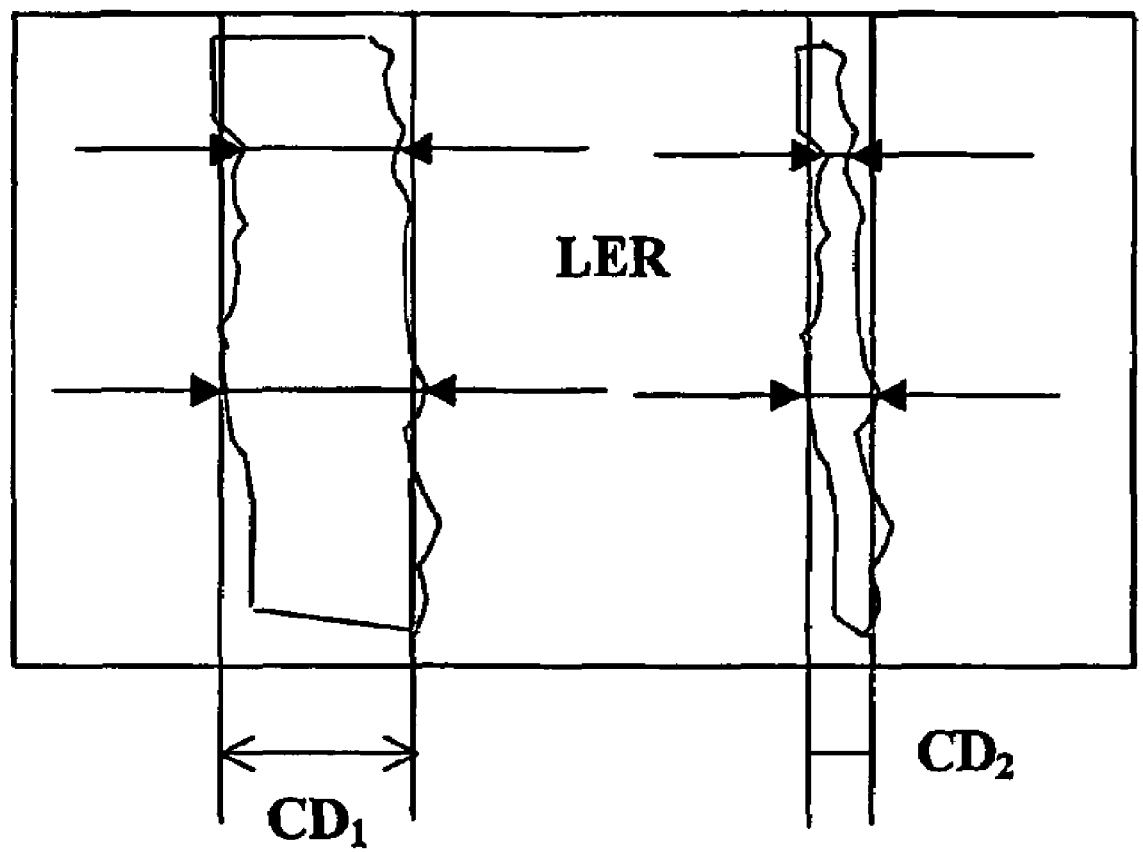
FIG. 1 is a schematic illustration of line edge roughness (LER) of two lines with different average CDs.
Figure 2:
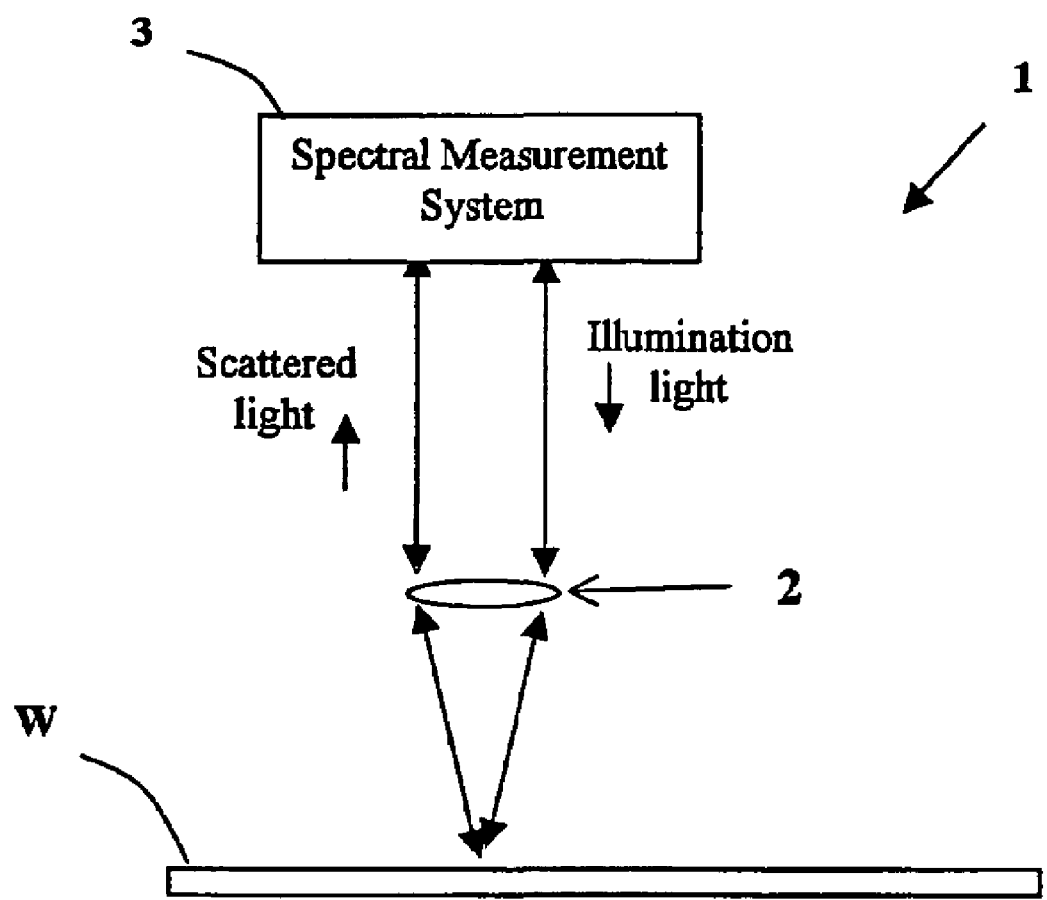
FIG. 2 is a schematic illustration of the main components of a measurement system constructed according to one embodiment of the invention, working in Bright Field (BF) mode, where signals from both regular features and LER component are collected in the same channel.

The following embodiments rely on the use of a spectroscopic measuring system (e.g. a normal incidence reflectometry system as shown in FIG. 2), which measures the reflectance or ellipsometric parameters of the diffraction from the sample. Such a measuring system will typically include the following elements: a light source (not shown), optionally a focusing element(s) such as lens 2 or mirror to focus the light to the sample, an aperture or some other means to limit the collection of light to a well-defined small area on the wafer, a detector 3, and optionally some means for navigation on the wafer W, such as an imaging channel and pattern-recognition soft- and/or hardware. Such embodiments work in Bright Field mode since the signal collected includes both a large component that is due to the regular nature of the sample (i.e. that would have been received from a sample with no LER), and a second, typically much smaller component due to the random nature of the sample (LER). Extracting the LER-related component is therefore not trivial and forms the main challenge in such an embodiment.

EXAMPLE 1

Using the Merit Function

The proposed measure of LER is based on the fact that LER, being a random effect, is not taken into account in rigorous models of diffraction, such as the Rigorous Couple Wave Analysis (RCWA). In this proposed method the first steps are identical to scatterometry, i.e. the spectra are measured from the sample and fitted to theoretical spectra calculated using a rigorous model. The assumption made is that fitting quality in the absence of LER is high (small average error), since all the parameters of the sample can be accurately taken into account. It is further assumed that LER is the major source for disagreement between the best fit and the measured spectra Under these assumptions we may conclude that residual differences between the best-fit and the measurement are evidence to the existence of LER In order to quantify the LER we may use a Merit Function (MF), which is some function of the measured and best-matched spectra, e.g. the standard deviation of the difference between two spectra. The same MF may also be the parameter that is minimized during the fitting procedure.

Additionally, it is possible to correlate between the MF and LER as measured by another technique (e.g. top SEM), e.g. using a controlled set of samples having variable LER but otherwise identical. Having established such correlation (for each specific application) we may use it as a calibration. Such a system, with or without an external calibration, will therefore be able to provide a non-destructive measurement of LER using an optical system (e.g. reflectometer, ellipsometer) allowing process alarm and/or process control.

EXAMPLE 2

Using Spectral Error Analysis

Another alternative to LER extraction from spectral measurements is to use the spectral difference between the measured spectrum and the best match. In difference from the previous solution, this measurement method does not relate only to the average error but rather on the spectral characteristics of the error.

Defining $S_m$ as the measured spectrum and $S_f$ its best fit using a rigorous model of the diffraction, we would like to spectrally analyze the residual error $S_{er}=(S_m-S_f)$.

A potential method to analyze the residual spectrum, given as an example, is to treat it as a vector in n-dimensional space, n being the number of wavelengths, and project this vector on the vectors formed by the spectral sensitivities of the different parameters.

For example, the spectral sensitivity to CD is defined by:

$$\delta S/\delta CD = (S(CD_0+\Delta CD)-S(CD_0))/\Delta CD$$

where S is the calculated spectrum at some point in parameter space.

We now define:

$$\delta CD = S_{er\_}*(\delta S\delta CD)$$

where the internal product (*) is defined as the integral over the spectrum of the wavelength-by-wavelength product of the two vectors. The result clearly has the dimensions of CD and may be interpreted, if the model is perfect otherwise, as the residual error in the determination of CD, which may than be correlated with the amount of the LER In a similar manner it is possible also to look at $\Delta A_w = S_{er\_}*(\delta S/\delta A_w)$ where $A_w$ is the wall angle, and likewise for other parameters.

EXAMPLE 3

Using a Model that Includes the Effect of LER

Another alternative to extract LER from specular measurements may be to use an extended model that takes into account in some way also the effect of LER Having such a model with free parameters describing both the regular grating and the LER distribution it would be possible to fit the measured spectra to such a model and get a direct measurement of LER.

Several methods to take into account LER could be considered:

(a) Use RCWA calculations with several values of CD (optionally: and various wall angles) and average them in order to take into account LER. The measure of LER would in this case be the range of CDs that has to be taken into account in order to get the best fit.

(b) Use RCWA with layers characterized by index of refraction that does not change abruptly on the walls but rather changes smoothly to take into account LER (this is a sort of effective mean field approximation which averages on the fluctuations).

(c) Since LER is a small perturbation to the overall structure, the spectrum with LER may be expected to behave as a superposition of the spectrum of the ideal profile and a component due to the random LER perturbation. The LER perturbation is expected to behave as an array of point scatterers, randomly distributed along the edges of the ideal profile. Standard scattering formalisms e.g. those used for aerosol scattering, may be applicable to this problem, with the appropriate modifications. Such a model will have to take into account that there are both negative and positive types of scattering centers, since the local index with LER may be either higher or lower than the ideal structure (in some locations line material instead of space material and in other locations the reverse). The model could also take into account the fact that the scatterers are randomly distributed along one axis only but are regularly spaced along the other axis. Additionally, the effect of the under-layers would have to be taken into account as it affects the local fields and thus the amount of scattered radiation.

The main drawback of all the abovementioned methods is that the "ideal" spectrum, due to the regular grating structure, is expected to be much larger than the deviation from the ideal case due to LEE In such cases the system might not be sensitive enough to correctly measure a small amount of LER.

LER Detection Methods Applying "Dark Field" Mode

The following methods are using additional optical elements in order to produce "dark field" measurement modes, in which the signal measured from an ideal, LER-free structure is expected to be zero (except system background and noise). Thus, every deviation from the ideal structure, i.e. even a small amount of LER, is expected to yield a detectable signal. Note: in all the sample embodiments shown below lenses are used as focusing elements, however equivalent implementations using mirrors as focusing elements can also easily be designed. The scope of this invention therefore includes all possible implementations of the proposed concepts, using both lenses and mirrors.

An additional, optional aspect of the present invention that is common to all the dark field methods presented below is the removal of background using a reference site. According to this aspect of the method the wafer is measured twice: both in a patterned site which is suspected to include LER and an additional, reference site, either un-patterned or patterned, that is not expected to include significant LER The net LER signal will be taken in this method as the difference between the two signals, measured on the two sites. Using this method it is possible to remove both system-related background signals and background signals related to scattering surfaces that are found below the upper layer. To some extent it is also possible to remove using this method scattering effects that are due to the bulk of the upper layer. Such scattering may be relevant when measuring post-etch lines of a multi-crystalline material, such as poly-Si. In order to remove bulk scattering it is required to use as a reference site a patterned site with the same duty cycle (line to period ratio) as the target site, however with a much larger period. Since the amount of line bulk material depends only on the duty cycle while the amount of LER-related scattering is expected to increase with the number of edges, i.e. inversely with the period, the net LER signal (after removing the reference site's signal) will not include bulk scattering effects if the period ratio between the two sites is sufficiently large.

EXAMPLE 4

Measuring Scattered Light

As described in Method 3, the LER may be regarded as a field of random scatterers, therefore, we should expect these scatterers to result in a wide-angle scattered light field, in contrast to the specular reflectance of an ideal grating (here we assume an ordered grating array scattering mainly to the zero order). By measuring the non-specular scattering intensity 9"dark field") it is therefore possible to get a direct measurement of the amount of scattering. Note, however, that one must also take into account that, depending on the grating period and measurement wavelength additional diffraction modes, on top of the specular, zero-mode diffraction, may be present It is therefore necessary to choose the collection angle range in a way that will guarantee that only scattered light could be collected.

There are several ways to implementation a dark-field measurement as an additional mode of operation on a scatterometry tool. The options described below refer specifically to a normal incidence scatterometry tool to which an additional mode of dark-field measurement is added. It is however also easily possible to modify the specifics of each of the options below to refer to an oblique-incidence system.

Figure 3:
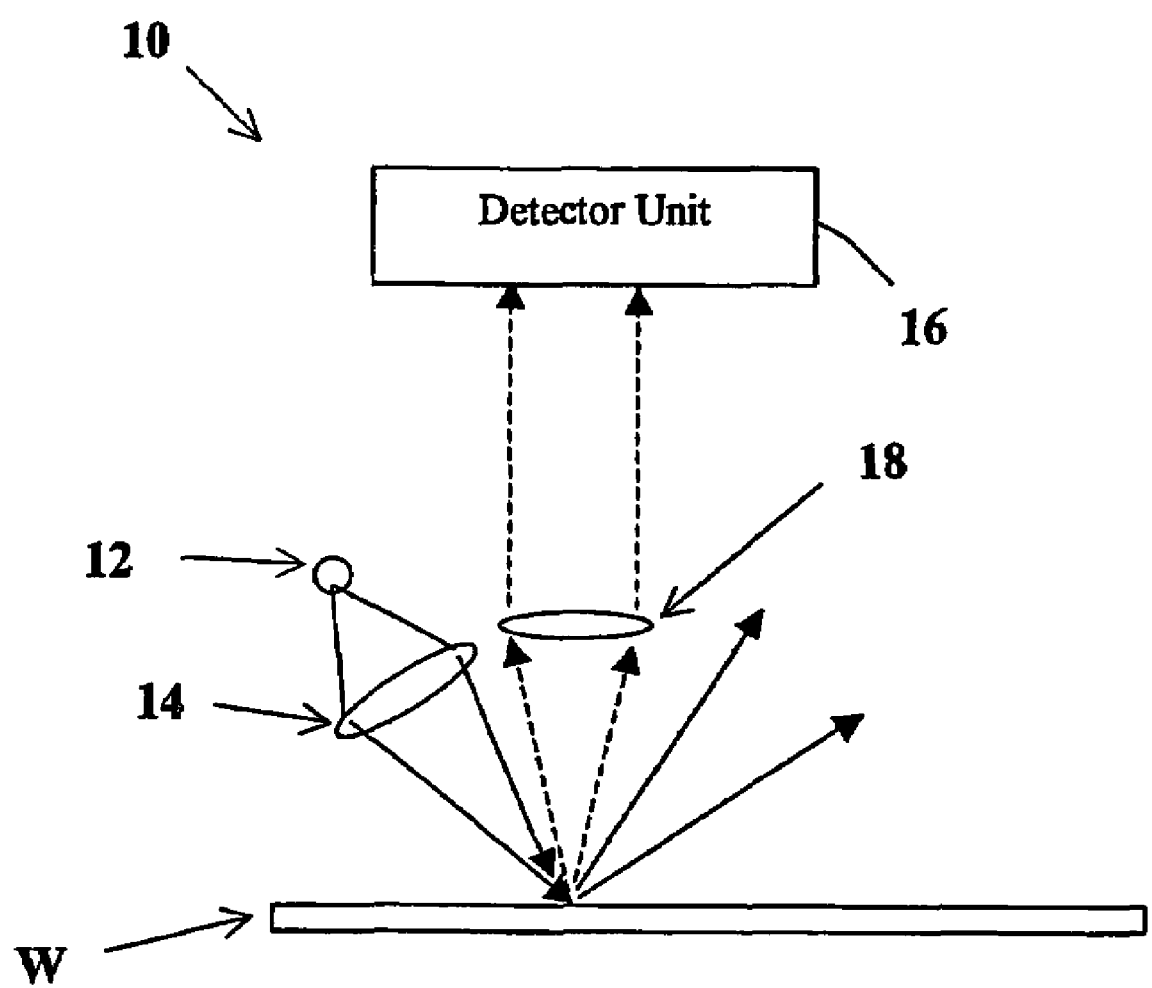
FIG. 3 is a schematic illustration of the main components of a measurement system constructed according to another embodiment of the invention, working in Dark Field (DF) mode, where for LER measurement the spectral measurement system performs only collection (no illumination) and a second, oblique illumination source is used.

One embodiment of such a system 10 is shown in FIG. 3. In accordance this embodiment the sample is illuminated using a special illumination source 12 and a focusing element 14 dens in the present example, but a mirror is also applicable) illuminating the sample at an incidence angle different than the normal incidence angle provided by the basic measurement system (in the case shown in FIG. 3—non-normal incidence). Most of the light is expected to reflect specularly from the sample (reflection angle equals incidence angle), however in the presence of LER it is expected that some of the light will be scattered also in other angles. In this embodiment the scattered light is measured by a detector unit 16 using the system's normal collection optical channel comprising a collection focusing element 18, lens in the present example (in FIG. 2—at normal angle to the sample). Detector unit 16 preferably comprises a spectrophotometer and imaging channel including a pinhole mirror, a relay lens and a pixel-array detector (e.g., CCD)—not shown.

Figure 4:
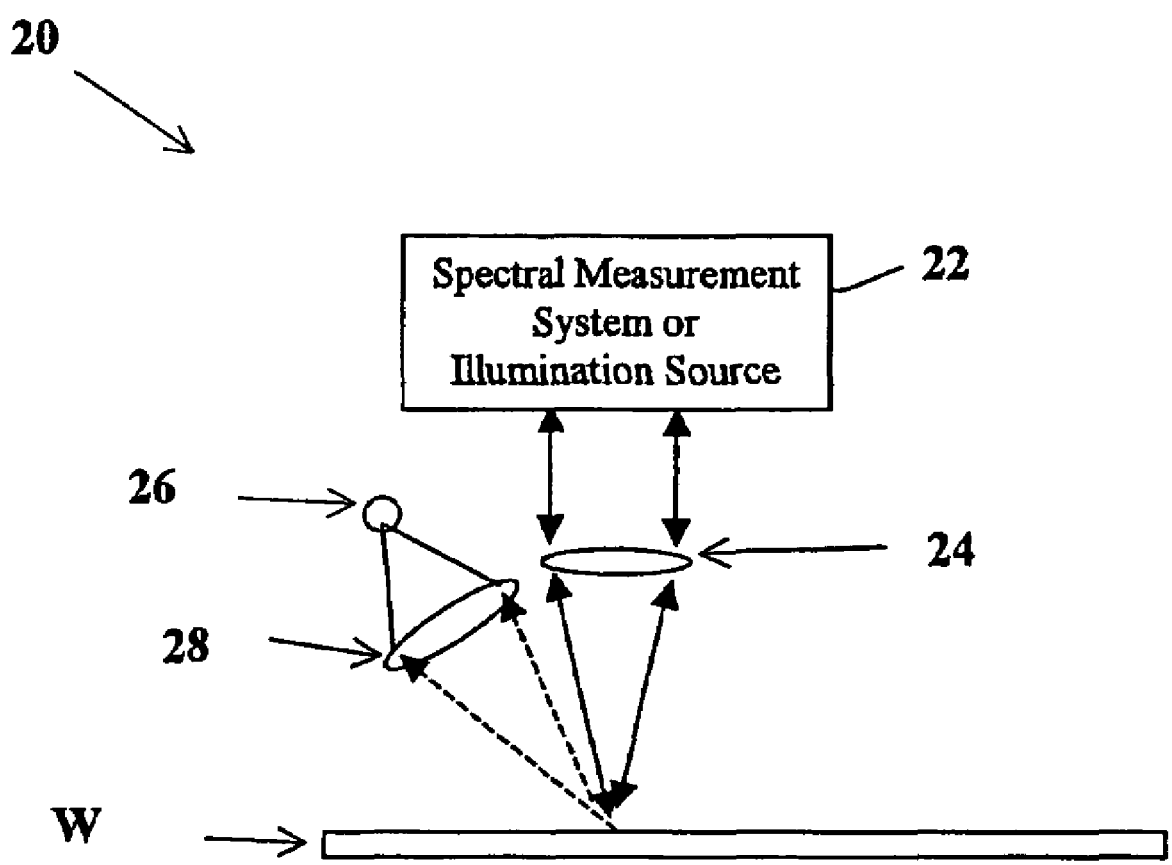
FIG. 4 is a schematic illustration of the main components of a measurement system constructed according to yet another embodiment of the invention, working in Dark Field (DF) mode, where for LER measurement the spectral measurement system performs only illumination (no collection) and a second, oblique spectral collection channel is used.

According to another embodiment of the present invention, shown in FIG. 4, a LER measurement system 20 comprises an illumination source 22 and focusing optics, e.g. lens 24 providing normal-incidence illuminating of the wafer. Detection of scattered light is done using a detector 26 based on special spectrometer or photo-detector and collection/focusing element 28, lens in the present example. Such LER measurement system 20 could be implemented as an additional unit of standard normal incidence spectroscopic measurement system (scatterometry tool)—see, for example the U.S. Pat. No. 6,045,433 assigned to the assignee of the present application. In that case the optical axis of LER detection optical channel oriented at some angle to the sample that is outside the regular incidence angle of the spectroscopic measurement system.

Figure 5:
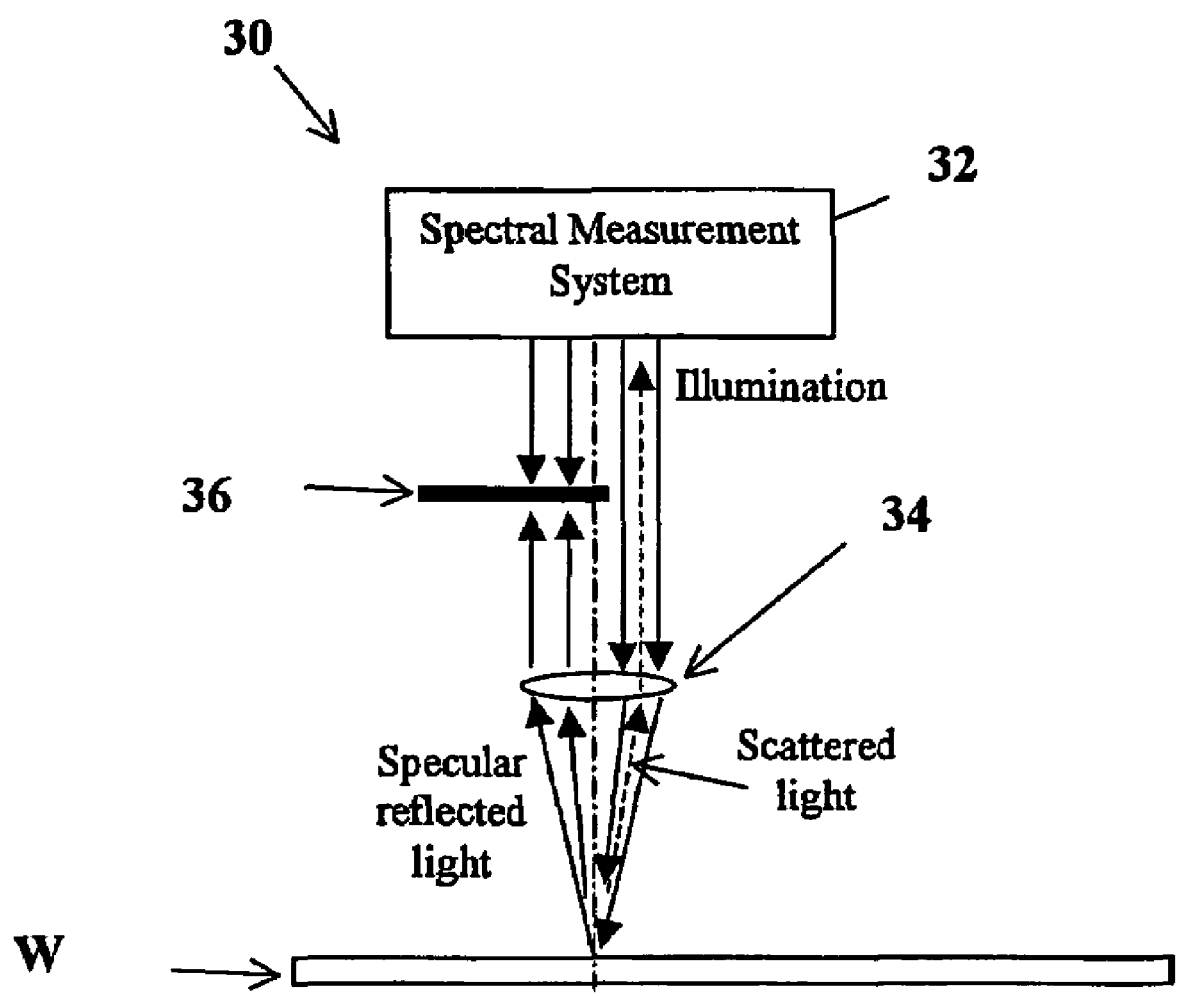
FIG. 5 is a schematic illustration of the main components of a measurement system constructed according to yet another embodiment of the invention, working in Dark Field (DF) mode, where in order to perform LER measurement a blocking screen is entered into the light path so as to block all or most of the specular reflection from the wafer, collecting mostly scattered light.

According to yet another embodiment of the present invention, shown in FIG. 5, the standard normal incidence spectroscopic system 30, comprising Illuminating/detection/ imaging arrangement 32 and focusing/collecting optics, a lens/s 34 in the present example is used for both illumination and LER detection. In order to create Dark Field effect the specular component is removed in this embodiment by blocking more than half of the system's aperture using a blocking screen or shutter 36 (e.g. as shown in the figure). Movable blocking screen 36 can be inserted only for LER measurements whereas otherwise the system 30 may be used for standard spectroscopic/scatterometry measurements in Bright Field mode.

Using either of the above embodiments of the system, once a net LER signal is detected there are two possibilities to utilize the signals detected: use the existence of any significant signal to operate a process alarm, or analyze the signals, find the quantitative magnitude of the LER and use it for process control. Analysis methods such as described in Method 3 may be used for this end.

EXAMPLE 5

Measuring Cross-Polarized Light

An additional expected effect of random scatterers is polarization mixing (as used in "Nomarski" mode in microscopes). When measuring an ideal grating using light which is polarized along one of its main directions (TE or TM) the symmetry of the structure ensures that no polarization mixing takes place, i.e. the reflected radiation has the same polarization as the illumination beam. However, the existence of random scatterers (i.e. line edge roughness) breaks the symmetry, therefore leading to polarization mixing. By measuring the component of cross-polarized light it may be possible to extract information regarding the LER.

Figure 6:
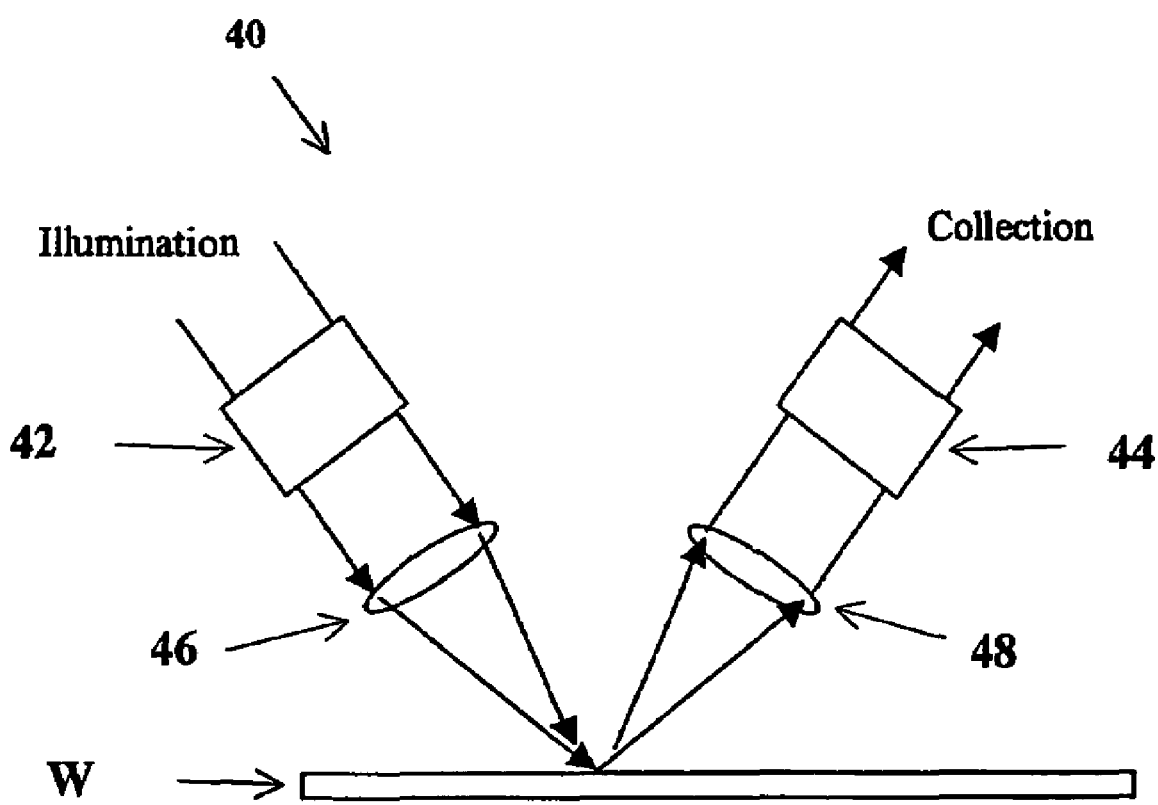
FIG. 6 is a schematic illustration of the main components of a measurement system acted according to yet another embodiment of the invention, working in Dark Field (DF) mode, where LER measurement is done by obliquely illuminating the wafer with light polarized in one direction and collecting light in another channel, in a different polarization.
Figure 7:
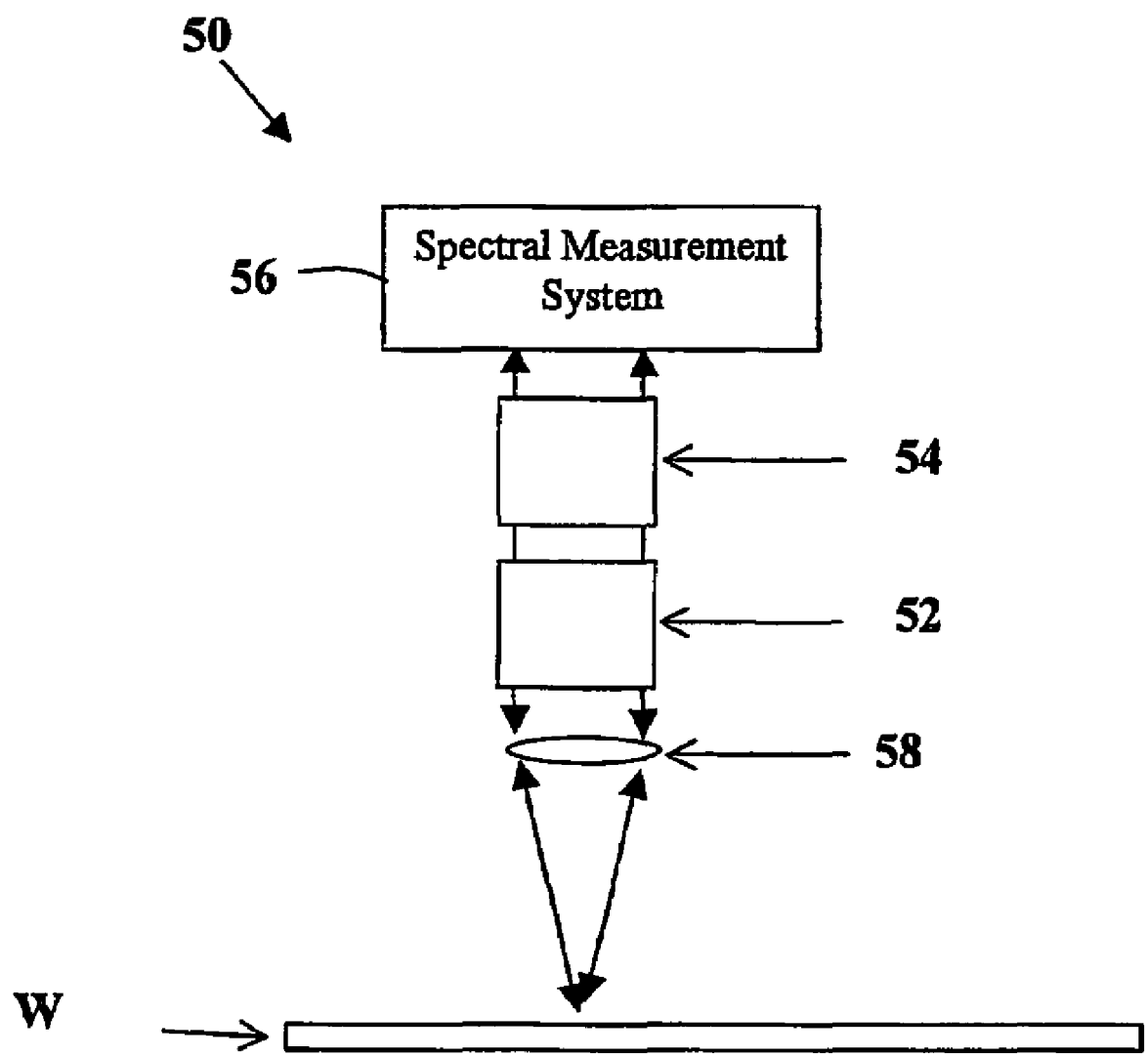
FIG. 7 is a schematic illustration of the main components of a measurement system constructed according to yet another embodiment of the invention, working in Dark Field (DF) mode, where LER measurement is done by changing the polarization of light going through a birefringence element such that the collected light is perpendicular in polarization relative to the illumination light.

According to one embodiment of this method an optical system is constructed as shown in FIG. 6. In this embodiment an oblique-incidence optical arrangement 40 uses polarizers 42 and 44 at both its arms, aligned such that illumination is done at either TE or TM (such that the light's electric field is either in the field of incidence or perpendicular to it) and the polarizer 44 at the collection arm (usually called "analyzer") is at a normal angle (90°) to the polarizer 42 at the illumination arm. Preferably, both arms of optical arrangement 40 comprise light focusing/collecting elements such as a lens 46 and 48. This arrangement, therefore measures the intensity of the component of light that has changed polarization during interaction with the sample. Since an ideal grating, illuminated in either TE or TM polarizations, is supposed to give zero cross-polarization, such a component can be attributed to LTR According to another embodiment of the present invention as shown in FIG. 7 a normal incidence system 50 is used in which a λ/4 retarding element 52 is placed in the light beam's path (illuminating and returned from the sample), after a stationary polarizer 54. In this embodiment only light that has changed its polarization state can return to the detector unit 56 since the beam is first polarized, than rotated by 45 degrees, interacts with the wafer, rotated by 45 degrees again on its way back and finally reaches again the polarizer 54. If the beam was reflected without any change in its polarization state that the accumulate 90 degrees shift results in blocking of the returning beam by the polarizer 54. Only that component that has changed its polarization state while interacting with the wafer will be able to pass the polarizer 54 and reach the detector unit 56. A retarding element 52 may be of any commonly known type, e.g. a Faraday rotator. The non-ideal nature of the retardation element 52 can be calibrated out by measuring a solid (un-patterned) site, for which cross-polarization is not expected to occur, and concerning the resulting signal as a result of the imperfection of the measuring system. Such a retardation element 52 could be inserted into the optical path only when required for this specific measurement mode while without this element the system may be used for normal incidence scatterometry. Preferably, the system 50 comprises light focusing/collecting elements such as a lens 58.

Again, using a model as discussed above to analyze the spectral dependence and the intensity of the cross-polarized field may allow an interpretation that does not require an experimental calibration.

Several different optional methods were presented for the detection and measurement of LER. Three of the methods rely on the "bright field" signal of a standard spectroscopy/scatterometry system, while the other two rely on an (additional) "dark field" channel or mode of operation, i.e. providing zero signal for the case of an ideal grating or solid (un-patterned) site.

Since the system should be able to detect small amounts of LER, scattering and polarization-mixing based methods, providing "dark field" type solutions, are expected to be more appropriate. Both these methods collect specific information since they allow measuring the spectral dependence of the measured effect from a small area of the wafer, defined by some aperture in the system. Therefore, the measurements of both methods can be either calibrated against external measurements of LER (e.g. top SEM) or analyzed using physical models, providing quantitative information regarding the nature of the distribution. Between these two methods, the preferred method should be chosen, among other things, according to the relative ease of implementation and therefore depends on the existing measurement system onto which LER detection has to be added.

Those skilled in the art will readily appreciate that various modifications and changes can be applied to the embodiments of the invention as hereinbefore exemplified without departing from its scope defined in and by the appended claims.

The invention claimed is:

1. A method of optical measurements of line edge roughness of patterned structures the method comprising:
    illuminating the structure with incident radiation and detecting a spectral response of the structure, applying software and/or hardware utilities for deriving information representative of said line edge roughness from said spectral response of the structure, wherein said hardware utilities comprises a bright field optical arrangement; and
    wherein applying of said bright-field optical arrangement further comprises step of blocking more than half of the optical arrangement aperture using a blocking shutter.

2. The method of claim 1 wherein said hardware utilities comprise a dark field optical arrangement.

3. The method of claim 2 wherein said dark field optical arrangement provides said illuminating the structure with normal incident radiation and detecting a scattered spectral response of the structure.

4. The method of claim 2 wherein said dark field optical arrangement provides said illuminating the structure with oblique incident radiation and detecting a normally scattered spectral response of the structure.

5. The method of claim 2 wherein said dark field optical arrangement further comprises a polarizer in an illuminating channel and analyzer in detecting channel, wherein axis of polarization said polarizer and analyzer are substantially mutually perpendicular.

6. The method of claim 1 wherein applying software and/or hardware utilities for deriving information representative of said line edge roughness from said spectral response of the structure comprises a merit function analysis.

7. The method of claim 1 wherein applying software and/or hardware utilities for deriving information representative of said line edge roughnessparameter/s from said spectral response of the structure comprises a spectral error analysis.

8. The method of claim 1 wherein applying softwareand/or hardware utilities for deriving information representative of said line edge roughnessparameter/s from said spectral response of the structure comprises applying a model including an effect of line edge roughness.

9. An optical measurement tool for line edge roughness of patterned structures comprising:

an illuminator for illuminating the structure with incident radiation and a detector for detecting a spectral response of the structure, and software and/or hardware utilities for deriving information representative of said line edge roughness from said spectral response of the structure, wherein said bright field optical arrangement further comprises in optical paths a blocking element for blocking more than half of the optical arrangement aperture.

10. The system of claim 9 wherein said hardware utilities comprises a dark field optical arrangement.

11. The system of claim 9 wherein said hardware utilities comprises a bright field optical arrangement.

12. The system of claim 11 wherein said optical arrangement further comprising in the optical paths a retarding element and a polarizer.

13. The system of claim 9 wherein said blocking element is in the form of an insertable shutter.

* * * * *